United States Patent [19]

Rohrer et al.

[11] 3,989,904

[45] Nov. 2, 1976

[54] METHOD AND APPARATUS FOR SETTING AN AURAL PROSTHESIS TO PROVIDE SPECIFIC AUDITORY DEFICIENCY CORRECTIONS

[75] Inventors: John S. Rohrer, Tempe; Vernon O. Blackledge, Scottsdale, both of Ariz.

[73] Assignee: John L. Holmes, Scottsdale, Ariz.

[22] Filed: Dec. 30, 1974

[21] Appl. No.: 537,066

[52] U.S. Cl. .................. 179/107 FD; 179/107 R
[51] Int. Cl.² ................ H04R 1/22; H04R 25/00
[58] Field of Search ......... 179/107 R, 107 FD, 1 A, 179/1 D, 1 N; 128/2 Z

[56] References Cited
UNITED STATES PATENTS

| | | | |
|---|---|---|---|
| 3,784,745 | 1/1974 | Stearns | 179/107 FD |
| 3,784,750 | 1/1974 | Stearns | 179/107 FD |
| 3,848,091 | 11/1974 | Stearns | 179/107 FD |

*Primary Examiner*—George G. Stellar

[57] ABSTRACT

Apparatus for setting or adjusting an aural prosthesis, such as a hearing aid, in order to provide compensatory amplification or attenuation for aurally handicapped persons such that the prosthesis compensates for the specific auditory deficiencies of that person. The apparatus includes a master hearing aid having one or more adjustable gain controls for determining the person's preferred word discrimination levels for a plurality of frequency bands. As the master hearing aid is set at the person's preferred level for each separate band, a reciprocal control coupled to each master control is adjusted at the same time. A hearing aid is then selected having an acuity deficiency correction characteristic generally similar to that determined by the previous test information, and that hearing aid is coupled to the reciprocal gain controls. The hearing aid selected is of a type which may have one or more adjustable filter networks and a maximum power output adjustment or any combination of one or more of these. Whatever adjustable controls the hearing aid may have for its filters or for maximum power output are then adjusted by reference to the reciprocal gain values so that the audio response curve of the hearing aid closely approximates that of the master hearing aid.

17 Claims, 4 Drawing Figures

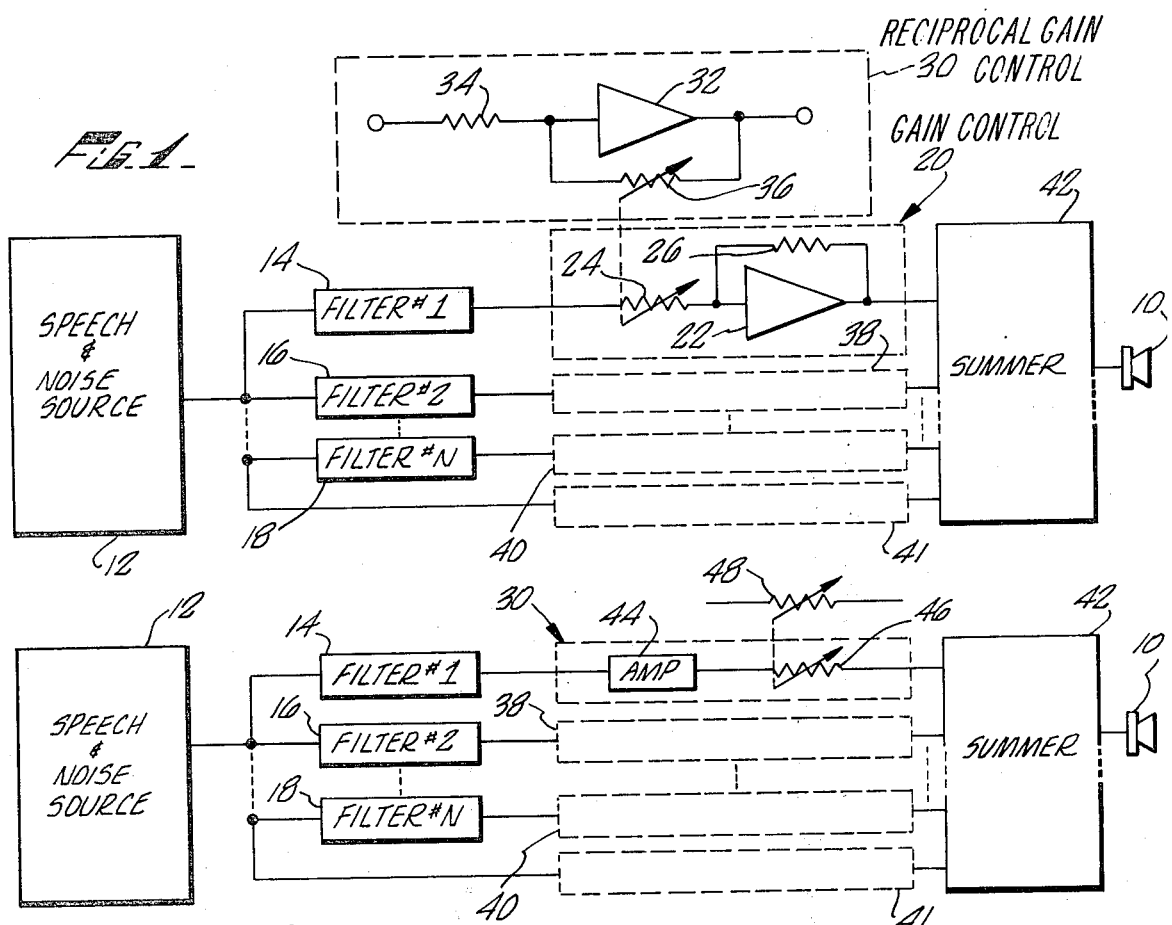
FIG. 1
FIG. 2
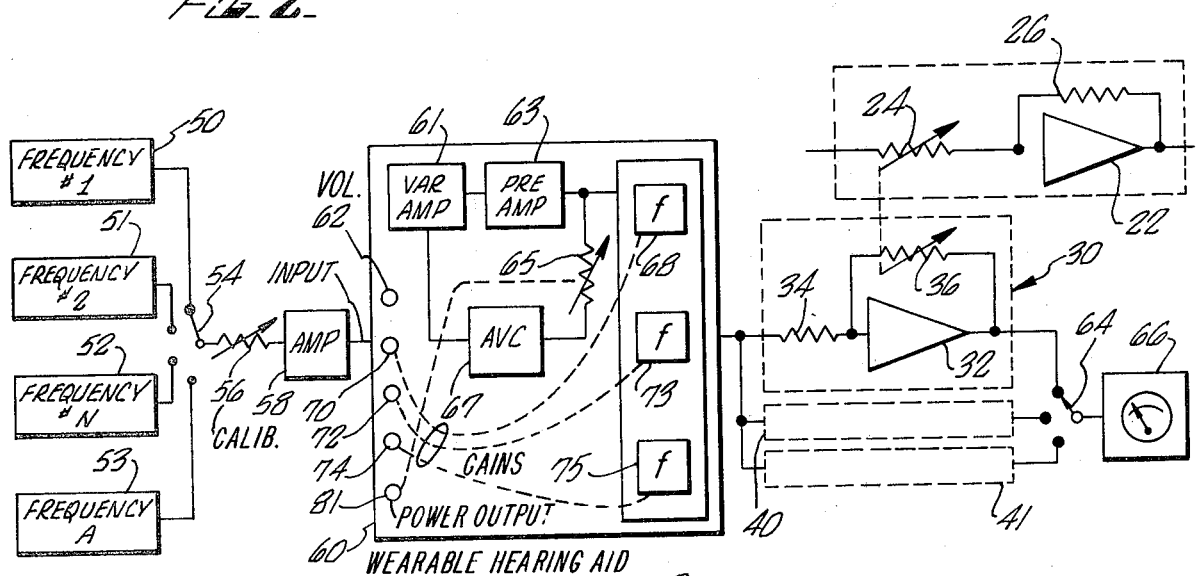
FIG. 3
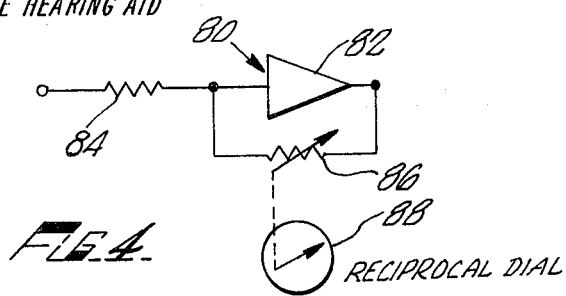
FIG. 4

METHOD AND APPARATUS FOR SETTING AN AURAL PROSTHESIS TO PROVIDE SPECIFIC AUDITORY DEFICIENCY CORRECTIONS

CROSS-REFERENCE TO RELATED APPLICATIONS

The present application is directed to inventive concepts which are related to those described in U.S. Pat. No. 3,784,745, issued Jan. 8, 1974, entitled "Method and Apparatus for Providing Electronic Sound Clarification for Aurally Handicapped Persons"; U.S. Pat. No. 3,784,750, issued Jan. 8, 1974, entitled "Apparatus and Prosthetic Device for Providing Electronic Correction of Auditory Deficiencies for Aurally Handicapped Persons"; U.S. Pat. No. 3,818,149, issued June 18, 1974, entitled "Prosthetic Device for Providing corrections of Auditory Deficiencies in Aurally Handicapped Persons"; and application Ser. No. 350,377, filed Apr. 12, 1973, in the names of William P. Stearns and Barry S. Elpern, entitled "Method of Fitting a Prosthetic Device for Providing Corrections of Auditory Deficiencies in Aurally Handicapped Persons", now U.S. Pat. No. 3,848,091 dated Nov. 12, 1974. All of the above-cited patents are assigned to the assignee of the present invention, and the disclosures thereof are incorporated herein by reference.

BACKGROUND OF THE INVENTION

This invention relates to the sound amplification arts and to their application in the amelioration of auditory deficiencies resulting from damage to the sensori-neural structure of the human ear. It relates particularly to apparatus for correcting deficiencies in a person's ability to perceive and to comprehend spoken language.

Sensori-neural hearing loss is generally considered to be the most prevalent type of auditory handicap found in the United States as well as in other civilized cultures. It constitutes a significant barrier to adequate communication in 5% to 10% of the total United States population and in more than 50% of the population over 60 years of age. Furthermore, these proportions are expected to increase in conjunction with ongoing increases in ambient noise levels and life expectancy in our society.

Sensori-neural impairment may result from any one or more of a number of causes including, but not limited to, genetic and congenital factors, viral diseases, specific toxic agents, circulatory disturbances, specific physical trauma and excessive exposure to noise. Irrespective of the primary cause, however, sensory cells within the organ of hearing or their associated neural units suffer some degree of damage and are rendered partially or totally incapable of fulfilling their respective roles in the processing of auditory information. This form of damage cannot be repaired by means of currently known medical or surgical techniques, and the probability of discovery of effective techniques, within the forseeable future appears rather remote. Thus, in virtually all cases of sensori-neural hearing loss, amplification of incoming sounds represents the only possible means for restoring adequate hearing ability.

Hearing loss resulting from sensori-neural damage is usually irregular with respect to frequency, being selectively greater for particular portions of the audible frequency range. The ability to hear sounds in the range above 1000 Hz is often affected more than the hearing of sounds below 1000 Hz, although this is by no means a universal observation. The ultimate consequency of irregular hearing acuity for various portions of the audio frequency spectrum is distortion in the perception of complex sounds, i.e., sounds composed of a number of different frequencies.

A certain amount of distortion in complex sounds may be tolerable, but current information does not permit precise specification of the maximum amount of each type of distortion which may exist without interfering materially with accurate sound recognition. Many gross sounds, for example, do not demand a great deal of analytic power in the auditory system, so even a rather severely impaired system may function adequately in the interpretation of such sounds.

In audiologic parlance, the term "discrimination" denotes the capacity of the ear to analyze incoming acoustic patterns and interpret them appropriately. Analytic power may fail at any of several stages in the auditory process, commonly in the organ of hearing or first order neurons due to damage to these structures. Since the ear may be required to perform many degrees of discrimination, varying from extremely coarse to extremely fine, its analytic power may be measured through the use of tests which demand auditory discriminations of progressive difficulty until failure occurs.

Among the most difficult discriminations required of the human ear are those necessary for accurate interpretation of speech, particularly speech in the presence of noise. Tests of speech discrimination are commonly employed, therefore, to derive a realistic estimate of a person's everyday functional adequacy in hearing.

Each of the phonic units of a spoken word is a complex sound, composed of several frequencies clustered in a more-or-less definable range. When the acuity of the ear has been selectively impaired in a specific frequency range, speech sounds or their components falling in that range may be heard at a reduced intensity or not at all. Impairment in several frequency ranges compounds the difficulty and is probably responsible in large measure for the primary complaint of the individual with sensori-neural hearing loss that he can hear a speaker's voice but cannot understand what is said. The mechanism for inhibiting such understanding may be the nonlinear responses that result in intermodulation products and harmonics which could cause interference with the desired spectral components of speech.

On the basis of the foregoing information, it would seem quite reasonable to deal with sensori-neural hearing loss by selective spectrum amplification; that is, providing amplification only in those frequency ranges or bands in which acuity is deficient, and only in the amount of the deficiency. Thus, the ultimate value of selective spectrum amplification rests on the application of appropriate methods for measuring the degree of auditory deficiency as a function of various frequency bands, and also on the construction of a wearable device which is fully capable of producing amplification to compensate for the measured deficiencies. Because of existing inadequacies in both respects, the principle of selective amplification has fallen into disrepute, for the hearing aid industry has adopted the pure tone (single frequency) threshold audiogram as the criterion measurement and has produced hearing aids with inadequate capabilities for providing proper acoustic output at each portion of the audio band.

The threshold audiogram curve represents an individual's measured absolute auditory threshold for a series of pure frequency tones, usually in the range of 250 Hz to 8000 Hz sampled at octave intervals on the assumption that intra-octave tone thresholds follow the general audiogram contour. However, it is demonstrable that fairly marked departures from this overall pattern may exist at intermediate frequencies, i.e., frequencies between pure tones one octave apart. In fact, careful consideration of the types of measurements which are genuinely helpful in guiding the design of particular hearing aid features suggests that the pure tone threshold curve is virtually useless for several reasons:

A. Under everyday circumstances, individuals react only to supra-threshold sounds, as these are sounds of primary significance. For practical purposes, threshold sounds remain unnoticed.

B. The contour of an individual's threshold curve is observably different from the contour of his supra-threshold equal loudness curves or comfortable listening level curves.

C. An individual's recognition of complex phonic units or their combination into spoken words is essentially unrelated to his acuity for individual pure tones.

Control of acoustic output in current hearing aids is ordinarily achieved through manipulation of frequency response, which refers to the acoustic output of a sound transmission system at each of the frequencies within its pass band when the input level is maintained constant for all frequencies. A graphic representation of a system's frequency response is referred to as a response characteristic, curve or contour. Manufacturers commonly claim that they are able to build hearing aids to yield any required frequency response; but this does not appear to be the case in practice because there are definite limitations on the band widths and response curves available in present day aids. In practice, manufacturers use combinations of components which produce a limited choice of response patterns and simply select one which most closely corresponds to the criterion, which, as mentioned earlier, usually is a threshold audiogram curve.

One additional comment is relevant as a preface to the innovative concepts to which the present invention is particularly addressed. It is generally recognized that the ear with sensori-neural hearing loss is excessively susceptible to overloading, which is to say that, although it may be relatively insensitive to sounds of low or moderate intensity, it is hypersensitive to sounds of higher intensity (i.e., nonlinear response characteristics). This condition restricts the useful operating range of the ear, referred to as the dynamic range; that is, the decibel difference between the lowest intensity at which a sound is reliably detected (absolute threshold) and the upper limit of comfortable loudness for that sound (discomfort threshold).

Whereas, the dynamic range of the normal ear is of the order of 100 dB, the range of a sensori-neurally impaired ear may be as little as 10 or 15 DB, generally over a limited frequency spectrum range. Thus, for an impaired ear to function with any degree of adequacy, the full intensity range of thet outside acoustic world must be restricted in some way to fit through an abnormally small sound window and such restriction must cause minimal intermodulation products, harmonics, and so forth which would result in distortion. Without such restriction, the ear is readily overloaded, leading to psychologic or physical annoyance and distortion of incoming acoustic patterns.

The consequences of overloading have been appreciated for many years, and output compression devices are widely used in today's hearing aids. Without exception, however, these devices operate on a broad frequency band, so that when any frequency component of a signal reaches a predetermined critical level, the entire pass band of the hearing aid is compressed. Consequently, the components which are not at a critical intensity are needlessly attenuated.

Our evaluation of relevant factors have led to the evolution of several innovative concepts providing improved methods and apparatus for measuring and defining auditory deficiencies in terms of a prescription for compenstory amplification, but then the remaining difficulty is the proper adjustment of the prosthetic device itself in order to assure that the prescribed compensatory amplification spectrum is operatively provided in the prosthetic device.

Modern wearable hearing aids vary considerably in circuitry and in the degree to which adjustments can be made in operating characteristics. Some have volume controls, maximum power output controls, some have no filter, others may have one or more filters, which provide frequency bands which may or may not be adjacent. In fact, in some hearing aids having multiple filters, one filter may provide a band which is completely or almost completely within the band of another filter. Even though gain controls may be provided for specific frequency bands, such devices are difficult to properly calibrate, particularly those aids worn entirely in or about the ear, they being quite small. Generally, no calibration indicia are provided for such devices, the adjusting screws are very small and are usually located inside a cover which must be removed in order to obtain access thereto. Adjusting a hearing aid while it is fitted to the patient's ear is considered a very unsatisfactory procedure as the very act of adjusting the tiny screws creates noises which are annoying to the patient. In addition to those problems, it is highly desirable to use unskilled or semiskilled labor for fitting hearing aids, and therefore a sufficiently simple and foolproof method and apparatus for incorporating the hearing profile prescription into the aid would be of considerable value.

SUMMARY OF THE INVENTION

It is a particular object of the present invention to provide apparatus such that hearing aids capable of compensatory amplitude and frequency adjustments can be fitted to a prescribed hearing curve by unskilled or semiskilled persons, specifically those engaged in the actual dispensing of such devices.

It is also an object of the present invention to provide simplified apparatus such that a patient's hearing curve can be ascertained by testing his hearing response for mixed inputs of speech and noise, obtaining preferred discrimination levels for each of the bands utilized, and then providing a means for selecting and matching the hearing aid itself to those tested levels without the necessity for complex electronic testing or measuring devices.

The foregoing objects of the present invention are realized by providing a testing apparatus in which the input signal is first divided into a plurality of frequency bands and then the gain is adjusted until the person undergoing the test indicates a preferred discrimination condition. The gain is adjusted by use of large controls by which fine adjustments can easily be made. As the gain is adjusted for each of the frequency bands, the adjusting mechanism provides a reciprocal gain adjustment which is set at the same time into the testing apparatus. Thereafter, an adjustable hearing aid device or prosthesis which is considered proper for the person is coupled to the reciprocal gain adjustment mechanism of the testing apparatus. The hearing aid includes an amplifier and may or may not include one or more filters, and it may or may not include a maximum power output device. The control for the maximum power output, the gain control of the amplifier and the gain control of the filters, if used, are adjusted until an equality is indicated on the testing apparatus whereby the hearing device is thereupon matched to the patient's tested hearing curve. It will be particularly noticed that, according to this invention, no reading is taken from the testing apparatus and remembered, or written down and then transferred manually to the prosthesis. On the contrary, the readings are stored mechanically or electrically by the setting of the reciprocal gain adjustments in the testing apparatus and the transfer of the test results from the testing apparatus to the prosthesis is electrical rather than manual.

BRIEF DESCRIPTION OF THE DRAWINGS

FIG. 1 is a block diagram illustrating an exemplary embodiment of the basic concepts of the present invention in which a master hearing aid is provided for initially determining the patient's hearing curve.

FIG. 2 is a block diagram of an alternate embodiment of the present invention utilizing analogous but somewhat distinct features.

FIG. 3 is a block diagram demonstrating the manner in which a wearable hearing aid is coupled to the testing apparatus for adjustment of the wearable aid to match the curve determined by the master hearing aid.

FIG. 4 is a partial circuit diagram of alternative embodiment of the present invention providing another means for setting the gain of the hearing aid to the reciprocal of the gain ascertained by the master hearing aid.

DESCRIPTION OF A PREFERRED EMBODIMENT

FIG. 1 represents schematically a master hearing aid device for empirically determining a person's hearing characteristics. A speaker 10 is inserted in the patient's ear and a mixture of speech and background noise is generated from source 12. As previously mentioned herein and as more specifically set forth in the previously issued patents referenced herein, the most useful hearing profile for a patient is determined by obtaining his discrimination responses to a mixture of spoken words heard in conjunction with background noise as this most accurately simulates the normal listening situation. The output from source 12 is then sent through a plurality of filters 14, 16 and 18. Filter 18 is designated filter "N" representing that the number of filters is not necessarily three, as shown in the drawings for the purposes of convenience of explanation, but in fact the number of filters can be more or less than three covering the audible frequency spectrum commencing from about 250 Hz to 8000 Hz in octave intervals.

The volume of sound passing through band pass filter 14 is controlled by gain control circuit generally designated 20 which includes an operational amplifier 22, a variable input resistor 24 and a fixed shunt resistor 26. As resistance 24 is increased, the overall gain of unit 20 is decreased, and vice versa. A reciprocal gain control unit 30 is associated with gain control unit 20 and consists of an operational amplifier 32 substantially similar in configuration to operational amplifier 22, except that amplifier 32 has a fixed input resistor 34 and a variable shunt resistor 36. Variable resistors 24 and 36 are mechanically coupled onto the same control shaft so that gain controls 20 and 30 are reciprocal and the sum of the gains in decibels is always the same. This is accomplished in that as resistor 24 is increased, for example, resistor 36 is so mounted that it is also increased. As the input resistor to amplifier 22 is increased, the gain decreases and, as the shunt resistor 36 is increased, the gain for amplifier 32 increases by the same amount.

At the initial testing stage of the master hearing aid unit, amplifier 32 is not in fact operational, but the shunt resistance is being adjusted in unison with the adjustment of the input resistor to amplifier 22. The gain control, therefore, of unit 20 is manipulated in the well-known manner until the patient indicates a preferred level of word discrimination. The output of filters 16 and 18 are likewise fed to similar gain control units 38 and 40, each of which is similarly coupled to a reciprocal gain control unit in the same manner as previously described, although these are not shown in the drawing. Suffice it to say that in each case, as the gain control units 20, 38 and 40 are adjusted, the reciprocal of the gain of each of those units is stored on each of the variable input resistors and, therefore, the reciprocal gain control units are thereby adjusted for future use. Each of the outputs from the gain control units 20, 38 and 40 is fed to a summer 42, the output of which supplies the speaker 10. Instead of feeding the input speech and noise from the source 12 simultaneously to all filter units, one can by appropriate switching feed the input sound to each of the filters separately.

For the maximum power output test, a gain control unit such as 41 may be used without a filter in its input. Desired maximum power in each filter pass band and/or overall maximum power may be determined by a suitable means, leaving the desired settings on the appropriate controls, similar to the gain settings.

FIG. 2 shows an alternative system closely resembling that shown in FIG. 1, except that in place of operational amplifiers, the gains are varied using attenuators. In FIG. 2, the output from filter 14 is passed to amplifier 44, the output of which is fed through a variable series resistor 46, the output of which then goes to the summer 42. The variable resistor 46 is similarly mechanically coupled to another resistor 48 as by being mounted upon the same control shaft, such that as resistor 46 is increased or decreased, resistor 48 is decreased or increased.

Turning now to FIG. 3, a system is shown for the setting of a wearable hearing aid in accordance with the audiological curve now set into the instrument as described with respect to FIG. 1. In FIG. 3, the system consists of a plurality of single frequency sources 50, 51 and 52 providing output signals of equal amplitude and having the frequencies of the filters 14, 16 and 18. Again, the number of sources 50–52 corresponds to the number of filters provided in the master hearing aid, as would be readily apparent, or a single variable source may be used. A selector switch 54 selects the output of one of the sources and, according to the method of the present invention, the dispensing audiologist selects that source having a frequency to which the person being fitted is least sensitive, in other words, the frequency at which the most gain is needed. The output of the selected frequency source is then applied through a calibrating resistor 56 and an amplifier 58, if necessary, to the input of the wearable hearing aid 60 to be adjusted. In this hearing aid, there are a number of adjustable elements, including a master volume control and individual gain controls for each pass band in that aid and possibly individual power output controls for each pass band and/or an overall power output control.

The hearing aid or prosthesis 60 is chosen by the dispensing audiologist to improve the hearing of the person as indicated to the audiologist by hearing tests and may include an amplifier but no filter or one or more filters which may or may not provide adjacent bands. In fact, in one type of hearing aid, a filter may provide a band pass that is wholly or nearly wholly within the pass band of another filter and either the wide or the narrow or both filters may be adjusted in this specification. The term "filter" includes any apparatus which alters the frequency response of the audio wave applied thereto. Also, as will be further explained, the prosthesis may contain power output controls 63, 67, 65 and the control 81 therefor.

The volume control 62 is first adjusted to maximum gain and all power output controls, such as 81, are set to maximum power output. The output of the hearing aid is then coupled to the inputs of the reciprocal gain control units, such as unit 30, and the same is true with respect to the other reciprocal gain control units as previously described in conjunction with FIG. 1. A selector switch 64 is coupled to the outputs of the reciprocal gain control units and to an indicator 66. In this configuration, with switch 64 selected to receive the output from the gain control unit corresponding to the frequency source previously selected by switch 54, then the corresponding filter 68, that is, the filter having the pass band corresponding to the selected source and the selected reciprocal gain control unit, is adjusted by means of an adjusting screw 70 to maximum gain and then the calibrating resistor 56 is adjusted until the indicator 66 reads a predetermined reference level. If measured in decibels (dB), the sum of the gain of the unit 30 and that provided by setting the screw 70 should have a predetermined value. The indicator 66 may be a meter or a blinking light or any device that indicates when a certain amplitude level is reached. This initial calibration having been accomplished, calibrating resistor 56 will not be changed again while setting the gains of the other filters of the wearable hearing aid 60.

Switch 54 is next turned to another frequency source, such as 51, and switch 64 is turned to the corresponding reciprocal gain control unit. Then, gain control 72 for filter 73 is adjusted until the indicator 66 reads the same as it did with the previous source. Again, switch 54 is turned to another frequency source, such as 52, selector switch 64 is again switched to the corresponding reciprocal gain control unit and then gain control unit 74 for filter 75 is adjusted until the indicator 66 again reads the same level. This sequence is repeated for each filter source. In this manner, hearing aid 60 is adjusted in accordance with the audiological profile prescribed by use of the master hearing aid of FIG. 1.

The maximum power output feature of the hearing aid 60 includes the elements 61, 63, 65 and 67. It will be noted that of these elements, elements 61, 63 and 67 comprise a known automatic gain control device, to which is added the variable resistor 65 in the feedback path of the automatic gain control device. This resistor 65 is varied by varying control 81.

To set the maximum power output, switch 54 is set to frequency source 53, which has an amplitude and frequency which will activate the power output mechanism associated with control 81. Control 81 is adjusted until indicator 66 shows that the desired level stored in unit 41 is reached. This process may be repeated for each power output control in the wearable hearing aid, if more than one is provided, with appropriate changes in the frequency of source 53.

It will be apparent that instead of using the system employing operational amplifiers, as set forth in FIG. 1, and the reciprocal amplifiers, as shown in FIG. 3, the reciprocal resistors 48 and amplifiers 44, as shown in FIG. 2, may be used in the same manner for adjustment of the pass band gains and the power output of the hearing aid.

As another variation of the present invention, a reciprocal operational amplifier 80, as shown in FIG. 4, may be provided as a separate piece of equipment not associated with the gain control units 20, 38 and 40 of the master hearing aid. The operational amplifier 80 is of similar configuration to those shown in FIG. 1, including an amplifier 82, input resistor 84 and a variable shunt resistor 86. The control shaft of variable resistor 86 is coupled to a reciprocally calibrated dial 88. The single operational amplifier 80 can then be used in a manner similar to that described with respect to FIG. 3, except that the single amplifier is used for setting the gain control of each of the frequency bands in the hearing aid 60. This is accomplished by taking the calibrated reading from the setting of resistor 24, for example, and by setting the reciprocally calibrated dial 88 to the same value, resistor 86 to automatically set so that amplifier 80 provides a gain which is the reciprocal of the gain of gain control unit 20. The same procedure can be followed for each of the gain control units by different settings of the reciprocal dial 88 for adjusting all of the frequency bands of hearing aid 60.

While particular embodiments of the present invention have been shown and described herein, such embodiments are to be considered in all respects as illustrative and not restrictive, and it will be apparent to those skilled in the art that many modifications, changes and alterations might be made within the scope of the invention without departing from its inventive concepts, and all changes which come with the meaning and range of equivalence of the claims therefore are intended to be embraced therein.

We claim:
1. Apparatus for adjusting an auditory prosthesis of the type having control means for controlling the volume thereof over at least part of the audible band, comprising:
   measuring means for establishing a person's auditory requirement over said part of the audible band, said measuring means including first gain control for controlling the gain of said measuring means over at least said part of the audible band, adjusting means responsively coupled to said first control means for adjusting the gain of said measuring means;
   second gain control means having variable means for adjusting the gain thereof, the adjusting means of said second control means being responsively coupled to the adjusting means of said first control means such that the gain of said second control means is always the reciprocal of the gain of the corresponding first control means; and input means for introducing audio frequency signals to said prosthesis, output means for receiving audio frequency signals from said prothesis, said second gain control means being electrically coupled to said output means, an indicating means, and means for coupling said second control means to said indicating means.

2. Apparatus for setting specific auditory corrections into an aural prosthesis of the type having an amplifier and an adjustable gain control for said amplifier, the combination comprising:

measuring means for establishing a person's audio discrimination capability within the audio frequency spectrum, said measuring means including first gain control means for controlling the gain of said measuring means, and means for adjusting said control means;

second gain control means having variable means for adjusting the gain thereof, the adjusting means of said second control means being responsively coupled to the adjusting means of said first control means such that the gain of said second control means is always the reciprocal of the gain of the corresponding first control means; and input means for introducing audio frequency signals to said prosthesis, output means for receiving audio frequency signals from said prosthesis, said second gain control means electrically coupled to said output means, an indicator means, and means for coupling said second control means to said indicator means.

3. Apparatus for setting specific auditory deficiency corrections into an aural prosthesis of the type having a filter means providing an audio pass band and an adjustable gain control for said pass band, the combination comprising:

means for establishing a person's audio discrimination capability within said pass band of the audio frequency spectrum, said measuring means including first gain control means for controlling the gain of said pass band, and means for adjusting the gain of said first control means;

second gain control means having variable means for adjusting the gain thereof, the adjusting means of said second control means being respectively coupled to the adjusting means of said first control means such that the gain of said second control means is always the reciprocal of the gain of the corresponding first control means; and input means for introducing audio frequency signals to said prosthesis, output means for receiving audio frequency signals from said prosthesis, said second gain control means electrically coupled to said output means, and indicator means, and means for coupling said second control means to said indicator means.

4. Apparatus for setting specific auditory deficiency corrections in an aural prosthesis of the type having a plurality of filter means providing audio pass bands and adjustable gain controls for each pass band, the combination comprising:

means receiving complex phonic input signals, filter means dividing said input signals into a plurality of discrete pass bands, first adjustable gain control means coupled to each of said filter means for adjusting the gain within each pass band;

second adjustable gain control means coupled to each of said first gain control means to form a pair, each pair of control means being simultaneously adjustable such that the gain of said second control means is always the reciprocal of the gain of said first control means; and means for introducing input signals to said prosthesis, said input signals corresponding in number to the number of filter means of said prosthesis and each having a characteristic audio frequency within one of the pass bands of said prosthesis, output means for receiving output signals from said prosthesis, said second gain control means being coupled to said output means, an indicator means, and selector means for selectively coupling said second gain control means to said indicator means.

5. Apparatus for setting specific auditory deficiency corrections in an aural prosthesis of the type having a plurality of filter means providing adjacent audio pass bands and adjustable gain controls for each pass band, the combination comprising:

means for establishing a patient's audio discrimination preferences within discrete pass bands of the audio frequency spectrum, said means including a plurality of filter means establishing said pass bands, first and second gain control means associated with each filter means, each of said first gain control means being operatively coupled to each filter means to control the gain in each pass band;

each said first and second gain control means further including adjusting means, the adjusting means of said first control means being operative to set the gain in each pass band for preferable aural discrimination, the adjusting means of each second control means responsive to the adjusting means of one of the first control means to always provide a gain which is the reciprocal of the gain of the first control means; and input means for selectively introducing audio frequency signals to said prosthesis, output means for receiving audio frequency signals from said prosthesis, said second gain control means electrically coupled to said output means, an indicator means, and selector means for selectively coupling said second control means to said indicator means.

6. Apparatus of the type described in claim 4 wherein said aural prosthesis includes two filter means each providing a band, the band of one of said filters being substantially completely included in the band of the other of said filters.

7. Apparatus of the type described in claim 1 wherein the input means to the prosthesis includes a series coupled variable calibrating resistor.

8. Apparatus of the type described in claim 4 wherein the input means to the prosthesis comprises means for generating the audio signals having frequencies within each of the pass bands of said prosthesis, first selector means for selectively introducing each of said audio signals to said prosthesis, and a variable calibrating resistor coupled in series to said selector means.

9. Apparatus of the type described in claim 2 wherein said measuring means further includes source means for introducing complex phonic signals, a plurality of filter means coupled to said source means for establishing discrete audio pass bands, said first gain control means comprising independent gain controls coupled to each of said filter means.

10. Apparatus of the type set forth in claim 9 wherein said measuring means further includes summation means coupled to each of said first gain control means, and a speaker coupled to said summation means.

11. Apparatus of the type described in claim 2 wherein:
said measuring means further includes source means for introducing complex phonic signals, a plurality of filter means coupled to said source means for establishing discrete adjacent audio pass bands, said first gain control means comprising independent gain controls coupled to each of said filter means; and
the input means to the prosthesis comprises means for generating audio signals having frequencies within each of the pass bands of said prosthesis, first selector means for selectively introducing each of said audio signals to said prosthesis, and a variable calibrating resistor coupled in series to said selector means.

12. Apparatus of the type described in claim 2 wherein:
said measuring means further includes source means for introducing complex phonic signals, a plurality of filter means coupled to said source means for establishing discrete adjacent audio pass bands, said first gain control means comprising independent gain controls coupled to each of said filter means, summation means coupled to each of said first gain control means, and a speaker coupled to said summation means; and
the input means to the prosthesis comprises means for generating audio signals having frequencies within each of the pass bands of said prosthesis, first selector means for selectively introducing each of said audio signals to said prosthesis, and a variable calibrating resistor coupled in series to said selector means.

13. Apparatus of the type described in claim 1 wherein said first and second gain control means each comprises an operational amplifier having an input resistor and a shunt resistor, the adjusting means of said first gain control means comprising a variable input resistor, the adjusting means of said second gain control means comprising a variable shunt resistor, each variable input resistor being coupled to one of said variable shunt resistors and simultaneously adjustable therewith.

14. Apparatus of the type described in claim 1 wherein said first and second gain control means each comprises a variable attenuator, the variable attenuator of each first gain control means being coupled to an attenuator of said second gain control means such that an increase in one attenuator causes a simultaneous decrease in the other.

15. Apparatus for setting specific auditory deficiency corrections in an arual prosthesis of the type having a plurality of filter means providing audio pass bands and adjustable gain controls for each pass band, the combination comprising:
input means for selectively introducing audio frequency signals to said prosthesis, output means for receiving audio frequency signals from said prosthesis, reciprocal gain control means electrically coupled to said output means, said reciprocal gain control means including means for adjusting the gain thereof, means calibrating said gain adjusting means in units reciprocal to the gain of a predetermined auditory deficiency correction, and means coupling said reciprocal gain control to indicator means.

16. The method of setting a specific auditory deficiency correction into an aural prosthesis of the type having at least one filter means providing an audio pass band and an adjustable gain control for said filter, the steps comprising:
measuring the gain required to provide a desired hearing discrimination within said pass band, providing the reciprocal of said measured gain and adjusting said gain control for said filter so that the sum of the gain of said filter and reciprocal of said measured gain in dB has a predetermined value.

17. The method of setting a specific auditory deficiency correction into an aural prosthesis of the type having at least two filter means each providing an audio pass band, the pass of one filter being substantially completely included within the pass band of the other filter and an adjustable gain control for said filters, the steps including:
measuring the gain required to provide a desired hearing discrimination within said pass bands;
providing the reciprocal of said measured gains; and
adjusting the gain control for said other filter so that the sum of the gain of said other filter and the reciprocal of said measured gain in dB has a predetermined value.

* * * * *